United States Patent
Zhang et al.

[11] Patent Number: 5,869,689
[45] Date of Patent: Feb. 9, 1999

[54] STAINS FOR ACIDIC ORGANELLES

[75] Inventors: Yu-Zhong Zhang; Zhenjun Diwu; Richard P. Haugland, all of Lane County, Oreg.

[73] Assignee: Molecular Probes, Inc, Eugene, Oreg.

[21] Appl. No.: 544,226

[22] Filed: Oct. 17, 1995

[51] Int. Cl.$^6$ .................................................. C07D 207/00
[52] U.S. Cl. ...................... 548/405; 548/110; 252/301.7; 372/39; 372/53; 372/54; 544/229
[58] Field of Search .................................. 548/110, 405; 252/301.7; 372/39, 53, 54; 544/229

[56] References Cited

U.S. PATENT DOCUMENTS

| | | |
|---|---|---|
| 4,774,339 | 9/1988 | Haugland et al. . |
| 4,916,711 | 4/1990 | Boyer et al. . |
| 5,187,288 | 2/1993 | Kang et al. . |
| 5,189,029 | 2/1993 | Boyer . |
| 5,248,782 | 9/1993 | Haugland et al. . |
| 5,274,113 | 12/1993 | Kang et al. . |
| 5,316,906 | 5/1994 | Haugland et al. . |
| 5,321,130 | 6/1994 | Yue et al. . |
| 5,326,692 | 7/1994 | Brinkley et al. . |
| 5,405,975 | 4/1995 | Kuhn et al. . |
| 5,410,030 | 4/1995 | Yue et al. . |
| 5,433,896 | 7/1995 | Kang et al. . |
| 5,436,134 | 7/1995 | Haugland et al. . |
| 5,437,980 | 8/1995 | Haugland et al. . |
| 5,442,045 | 8/1995 | Haugland et al. . |
| 5,443,986 | 8/1995 | Haugland et al. . |
| 5,446,157 | 8/1995 | Morgan et al. . |
| 5,451,663 | 9/1995 | Kang et al. . |
| 5,453,517 | 9/1995 | Kuhn et al. . |
| 5,459,268 | 10/1995 | Haugland et al. . |
| 5,573,909 | 11/1996 | Singer et al. . |
| 5,614,386 | 3/1997 | Metzker et al. . |
| 5,648,270 | 7/1997 | Kuhn et al. . |

FOREIGN PATENT DOCUMENTS

WO 93/06482  4/1993  WIPO .

OTHER PUBLICATIONS

Verhoef, et al., J. Immunology 131, 125 (1983).
Vandenbroucke–Grauls, et al., Immunology 51, 319 (1984).
Biederbick, et al., Eur. J. Cell Biol. 66, 3 (1995).
Treibs & Kreuzer, Liebigs Ann. Chem. 718, 208 (1968).
Müller, et al., Monatshefte für Chemie 116, 365 (1985).
Geze, et al., J. Photochem. Photobiol 20, 23–35 (1993).
Berg, et al., Int. J. Cancer 59, 814–822 (1994).
"Molecular Aspects of Anticancer Drug Action", Neidel and Waring, Eds., Macmillan, London; pp. 233–286 (1983).

*Primary Examiner*—James O. Wilson
*Attorney, Agent, or Firm*—Allegra J. Helfenstein; Anton E. Skaugset

[57] ABSTRACT

Dipyrrometheneboron difluoride dyes possessing a covalently attached basic amine moiety are described that have utility for staining acidic organelles. Samples comprising isolated acidic organelles, or a cell or cells containing acidic organelles, are stained by preparing an aqueous labeling solution of the dye and incubating the sample in the labeling solution for a time sufficient to produce fluorescent labeled acidic organelles.

30 Claims, No Drawings

STAINS FOR ACIDIC ORGANELLES

FIELD OF THE INVENTION

The invention relates to the fluorescent staining of acidic organelles, whether in cells, or isolated from cells. The fluorescent organelle stains of the invention are selectively sequestered in acidic organelles, such as lysosomes, rendering the organelles fluorescent and easily observed.

BACKGROUND OF THE INVENTION

The present invention utilizes fluorescent acidotropic probes for the labeling and tracing of acidic organelles in cells and cell-free systems. Acidotropic probes selectively accumulate in cellular compartments with low internal pH and can be used to investigate the biosynthesis and pathogenesis of lysosomes in cultured animal cells.

While some weakly basic amines have been shown to selectively accumulate in cellular compartments with low internal pH, there have been relatively few acidic organelle stains available for the researcher. The most frequently used acidotropic probe, N-(3-((2,4-dinitrophenyl)amino)propyl)-N-(3-aminopropyl)methylamine, dihydrochloride (hereafter referred to as DAMP), is not fluorescent and requires fixation and permeabilization of the cell, followed by the use of anti-DNP antibodies conjugated to a fluorophore, an enzyme or ferritin in order to visualize the staining pattern. The fluorescent probes neutral red and acridine orange are also commonly used for staining acidic organelles, but they lack specificity and are not well retained in the organelles, particularly after fixing and permeabilization.

The compound dansyl cadaverine has been described as a lysosomotropic reagent (Verhoef, et al. J. IMMUNOLOGY 131, 125 (1983); Vandenbroucke-Grauls, et al. IMMUNOLOGY 51, 319 (1984)), however dansyl cadaverine is only described as having an effect on the function of human natural killer cells and human polymorphonuclear leucocytes. More recent research describes monodansyl cadaverine as a fluorescent label, however it is described as useful as a label for autophagic vacuoles, as it fails to label either endosomal compartments or lysosomes (Biederbick et al. EUR. J. CELL BIOL. 66, 3 (1995). In addition, monodansyl cadaverine possesses several additional disadvantages. The dansyl fluorophore is excited in the ultraviolet region (<350 nm), which is generally incompatible with living systems, has a low quantum yield and has a low extinction coefficient (less than 5,000) requiring high concentrations of dye when staining cells.

The method of the present invention stains acidic organelles rapidly and brightly, and is useful for both short-term and long-term tracking studies. The dyes used in the current method are highly selective for acidic organelles, label living cells at submicromolar concentrations of probe, and exhibit bright fluorescent staining and good photostability. In addition, many of the dyes of the invention are well-retained in acidic organelles, even after aldehyde fixation. The current invention uses a dipyrrometheneboron difluoride fluorophore linked to a weak base that is only partially protonated at neutral pH.

Certain characteristics of dipyrrometheneboron difluoride dyes are known. The fluorescence of simple substituted dipyrrometheneboron difluoride derivatives, comparable to that of fluorescein, was previously noted by Treibs & Kreuzer (*Difluorboryl-Komplexe von Di- und Tripyrrylmethenen,* LIEBIGS ANN. CHEM. 718, 208 (1968)). Use of such dyes for dye laser systems is described in U.S. Pat. No. 4,916,711 to Boyer, et al. (1990) (incorporated by reference). The use of simple dipyrrometheneborondifluoride dyes as sensitizing agents to enhance photodynamic therapy (PDT) has been specifically described by Boyer (U.S. Pat. No. 5,189,029; incorporated by reference). Chemically reactive dipyrrometheneboron difluoride dyes that can be coupled to other molecules are described in U.S. Pat. No. 4,774,339 to Haugland, et al. (1988) (incorporated by reference). This patent describes dipyrrometheneboron difluoride dyes that possess high quantum yields, insensitivity of fluorescence properties to changes in pH, high absorbance, and a broad range of solubilities. The references, however, do not describe the utility of dipyrrometheneboron difluoride dyes that possess a weakly basic amine moiety for preferentially staining acidic organelles. Haugland et al. (1988) fails to specifically describe dipyrrometheneboron difluoride dyes having substituents that are in turn substituted by tertiary aliphatic amines, primarily as the reference is describing chemically reactive fluorophores, and a tertiary amine is not typically considered to be a chemically reactive group, in the sense of being useful for preparing labeled conjugates.

More recently, additional dipyrrometheneboron difluoride dyes with advantageous long-wavelength characteristics have been identified, including ethenyl-substituted dipyrrometheneboron difluoride dyes as described in U.S. Pat. No. 5,187,288 to Kang et al. (1993) (incorporated by reference); heteroaryl-substituted dipyrrometheneboron difluoride dyes as described in U.S. Pat. No. 5,248,782 to Haugland, et al. (1993) (incorporated by reference); and aza-dipyrrometheneboron difluoride dyes as described in U.S. Pat. No. 5,446,157 to Morgan et al. (1995) (incorporated by reference). In addition, chemically reactive long wavelength dyes have been described in U.S. Pat. No. 5,274,113 to Kang, et al. (1993) (incorporated by reference); and benzo-substituted dipyrrometheneboron difluoride dyes as described in U.S. Pat. No. 5,433,896 to Kang, et al. (1995) (incorporated by reference). While the preparation of amino and aminoalkyl substituted dyes were described in the above patents, none of the patents describe the utility of such compounds particularly for preferentially staining acidic organelles. The above patents that are directed at reactive dyes also fail to describe dyes having substituents that are in turn substituted by tertiary aliphatic amines, as tertiary amines are typically not considered to be chemically reactive groups. Previously, primary aminoalkyl substituents have typically been utilized to provide a site for conjugating the dipyrrometheneboron difluoride dye to a desired biomolecule.

The acidic organelle stains of this invention are freely permeant to membranes of intact cells and can be used for staining cells at very low concentrations of dye that are not toxic to living cells or tissues. The instant dyes and method are useful for investigating the biogenesis of lysosomes, the development of autophagic vacuoles, investigating retina and cultured neurons, and detecting pH gradients. The current invention is also useful for labeling cells that possess acidic organelles, such as yeast, spermatozoa and plant cells.

SUMMARY OF THE INVENTION

The present invention includes a method and materials for staining acidic organelles, whether present in cells or as isolated cell-free organelles, with a fluorescent dye. The method comprises: preparing a labeling solution containing a fluorescent stain, where the fluorescent stain comprises a substituted or unsubstituted dipyrrometheneboron difluoride dye possessing a covalently attached basic amine moiety; and incubating a sample comprising isolated acidic organelles, or a cell or cells containing acidic organelles, in the labeling solution for a time sufficient to produce fluorescent labeled acidic organelles. The use of the acidic organelle stains of the invention are optionally combined with the use of an additional detection reagent. The stained acidic organelles are optionally observed using a means for detecting the fluorescent signal, and optionally sorted.

DESCRIPTION OF THE PREFERRED EMBODIMENTS

The acidic organelle stains of the present invention are dipyrrometheneboron difluoride dyes having the formula

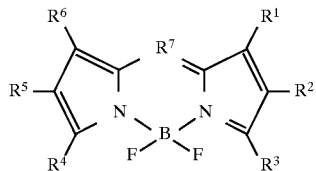

where the substituents $R^1$–$R^6$, which may be the same or different, are hydrogen, halogen, cyano, alkyl, perfluoroalkyl, alkoxy, cycloalkyl, arylalkyl, acyl, aryl, heteroaryl, alkenyl or alkynyl; or a LINK-CAP moiety. The bridging $R^7$ is optionally a nitrogen atom, yielding an aza-dipyrrometheneboron difluoride dye, or $R^7$ is a methine (—CH═) or a methine that is substituted by halomethyl, cyano, alkyl, perfluoroalky, alkenyl, alkynyl, cycloalkyl, arylalkyl, acyl, aryl, heteroaryl, or a LINK-CAP moiety. Preferably $R^7$ is a methine or substituted methine. Where $R^7$ is a substituted methine, preferably the substituents are halomethyl or a LINK-CAP moiety.

Preferably, the substituents $R^1$–$R^6$ that are not a LINK-CAP moiety are hydrogen, halogen, alkyl, aryl, heteroaryl or alkenyl. More preferably, the substituents $R^1$–$R^6$ that are not a LINK-CAP are hydrogen, halogen or alkyl. Alternatively, for those dyes where $R^7$ is not nitrogen, any two adjacent substituents of $R^1$, $R^2$, $R^3$, $R^4$, $R^5$ and $R^6$, taken in combination, form a fused aromatic 6-membered ring that is optionally and independently substituted one or more time, at any position, by halogen, cyano, alkyl, perfluoroalkyl, alkoxy, alkenyl, alkynyl, cycloalkyl, alkylthio, alkylamido, amino, monoalkylamino, dialkylamino, carboxamide, hydroxy, mercapto, aryl, heteroaryl, aryl-amido, heteroaryl-amido, aryl-oxy, heteroaryl-oxy, aryl-amino, or heteroaryl-amino, or 1–2 additional fused benzo or heteroaromatic rings that are themselves optionally further substituted by halogen, amino or carboxamide. Any of the fused aromatic 6-membered rings or additional fused benzo or heteroaromatic rings is optionally substituted one or more times by a LINK-CAP moiety.

As used herein, aryl is an aromatic or polyaromatic substituent containing 1 to 4 aromatic rings (each ring containing 6 conjugated carbon atoms and no heteroatoms) that are optionally fused to each other or bonded to each other by carbon-carbon single bonds. Each aryl is bound to the dye by a single bond, and is optionally substituted as described below.

As used herein, a heteroaryl is an aromatic group that contains at least one heteroatom (a non-carbon atom within the ring structure). Each heteroaryl is a single 5- or 6-member ring, or is a fused 2- or 3-ring structure. The heteroaryl group contains one or more heteroatoms, e.g. as pyrrole, thiophene, or furan (single ring, single heteroatom), or oxazole, isoxazole, oxadiazole, or imidazole (single ring, multiple heteroatoms), or benzoxazole, benzothiazole, or benzimidazole (multi-ring, multiple heteroatoms), or benzofuran or indole (multi-ring, single heteroatom). Each heteroaryl is bound to the dye by a single bond, and is optionally substituted as described below.

Any aryl, heteroaryl, aryl-amido, heteroaryl-amido, aryl-oxy, heteroaryl-oxy, aryl-amino or heteroaryl-amino substituent on the dye itself, or present on a substituent, is optionally and independently substituted one or more times by halogen, amino, carboxamide, hydroxy or mercapto.

Any of said alkenyl or alkynyl substituents independently has 2–6 carbons, and is optionally substituted by halogen, alkyl, cyano, carboxylate ester, carboxamide, aryl, heteroaryl, or additional alkenyl or alkynyl groups. Preferably an alkenyl group is an ethenyl, dienyl or trienyl group.

Each of the alkyl substituents, as well as the alkyl portions of alkoxy, cycloalkyl, arylalkyl, alkylamino, alkylthio or alkylamido substituents independently has 1–6 carbons, and is optionally substituted by halogen, amino, alkylamino, dialkylamino, carboxamide, hydroxy, mercapto or cyano.

For all embodiments, at least one of $R^1$–$R^6$ is a LINK-CAP moiety, or $R^7$ is a LINK-CAP substituted methine, or one of the dye substituents that is a fused 6-membered ring is further substituted by a LINK-CAP moiety. For all embodiments, where the dye is substituted by more than one LINK-CAP, they are the same or different.

The LINK portion of LINK-CAP is a covalent linkage, serving to attach a weakly basic amine, CAP, to the dipyrrometheneboron difluoride fluorophore itself. Any suitable covalent linkage that does not interfere with the ability of the dye to selectively accumulate in acidic organelles is an acceptable covalent linkage for the purposes of the present invention. In one embodiment, LINK is a single covalent bond. Preferred LINK groups have 1–20 nonhydrogen atoms selected from the group consisting of C, N, O and S. Such LINK groups are composed of any combination of chemical bonds, including ether, thioether, amine, ester, carboxamide, sulfonamide, hydrazide bonds, and single, double, triple carbon-carbon bonds, and aromatic or heteroaromatic bonds. Preferred LINK groups are composed of any combination of single carbon-carbon bonds and carboxamide bonds. Selected specific examples of LINK optionally include methylenes, oligomethylenes, phenylenes, thienyls, carboxamides, and sulfonamides. In one embodiment of the invention, LINK contains 1–6 carbon atoms. In an additional embodiment of the invention, LINK has the formula —$(CH_2)_a(CONH(CH_2)_b)_z$—, where a has any value from 0–5, b has any value from 1–5 and z is 0 or 1.

CAP has the general formula —$CR^8R^9$—$NR^{10}R^{11}$. The substituents $R^8$ and $R^9$ are independently hydrogen or alkyls having 1–6 carbons that are linear or branched. Typically, $R^8$ and $R^9$ are hydrogen or alkyls having 1–2 carbons, more preferably both $R^8$ and $R^9$ are hydrogen. Where $R^8$ or $R^9$ are alkyl groups, each alkyl group is optionally further substituted by halogen, carboxamide, hydroxy, mercapto or cyano. In addition, any alkyl group is optionally further substituted by a primary, secondary or tertiary amine, where the alkyl groups present on the amine independently have 1–6 carbons. In an additional embodiment of the invention, one of $R^8$ and $R^9$, when taken in combination with the LINK moiety, forms a six- to eight-membered ring.

The amine substituents $R^{10}$ and $R^{11}$ are each independently H or a linear or branched alkyl having 1–6 carbons. Alternatively, $R^{10}$ and $R^{11}$, when taken in combination form a nitrogen heterocycle that preserves the basic nature of the amine nitrogen. Preferably, the nitrogen heterocycle is a pyrrolidine, a piperidine, a piperazine, morpholine, an imidazole, an azepine (including diazepines and triazepines) or an oxazepine. In another embodiment of the invention, the amine substituents $R^{10}$ and $R^{11}$, when taken in combination with substituents $R^8$ and $R^9$, or with the LINK moiety, form a saturated five- or six-membered nitrogen heterocycle that is a substituted pyrrolidine or piperidine.

For all embodiments of the invention, the basic CAP moiety is optionally present in the form of a salt of a strong acid, for example the hydrochloride salt, sulfate salt, perchlorate salt, or other organic acid salts.

Selected specific embodiments of dyes useful for the staining of acidic organelles are described in Tables 1 and 2:

TABLE 1

Selected Embodiments of the Dyes of the Invention

[Structure: BODIPY core with substituents $R^1$, $R^2$, $R^3$, $R^4$, $R^5$, $R^6$, $R^7$ around pyrrole-BF$_2$-pyrrole system]

| Dye No. | $R^1$ | $R^2$ | $R^3$ | $R^4$ | $R^5$ | $R^6$ | $R^7$ |
|---|---|---|---|---|---|---|---|
| 1 | H | H | (CH$_2$)$_2$CONH—(CH$_2$)$_2$NH$_2$ | Me | H | Me | CH |
| 2 | H | H | (CH$_2$)$_2$CONH—(CH$_2$)$_2$NHMe | Me | H | Me | CH |
| 3 | H | H | (CH$_2$)$_2$CONH—(CH$_2$)$_2$NMe$_2$ | Me | H | Me | CH |
| 4 | H | H | (CH$_2$)$_2$CONH—(CH$_2$)$_2$N(Et)$_2$ | Me | H | Me | CH |
| 5 | H | H | (CH$_2$)$_2$CONH—(CH$_2$)$_2$N(Pr)$_2$ | Me | H | Me | CH |
| 6 | H | H | (CH$_2$)$_2$CONH—(CH$_2$)$_2$N(Bu)$_2$ | Me | H | Me | CH |
| 7 | H | H | CH$_2$N(morpholine: N—(CH$_2$CH$_2$)$_2$—O) | Me | H | Me | CH |
| 8 | H | H | (CH$_2$)$_2$SO$_2$NH—(CH$_2$)$_2$NH$_2$ | Me | H | Me | CH |
| 9 | H | H | (CH$_2$)$_2$SO$_2$NH—(CH$_2$)$_2$N(Me)$_2$ | Me | H | Me | CH |
| 10 | H | H | (CH$_2$)$_3$NH$_2$ | Me | H | Me | CH |
| 11 | H | H | CH$_2$N(Me)$_2$ | Me | H | Me | CH |
| 12 | H | H | CH$_2$NH$_2$ | Me | H | Me | CH |
| 13 | H | H | (CH$_2$)$_3$NH—(CH$_2$)$_3$N(Me)$_2$ | Me | H | Me | CH |
| 14 | H | H | (CH$_2$)$_3$NH—(CH$_2$)$_2$N(Bu)$_2$ | Me | H | Me | CH |
| 15 | H | H | (CH$_2$)$_3$NHCSNH—(CH$_2$)$_2$N(Me)$_2$ | Me | H | Me | CH |
| 16 | H | H | (CH$_2$)$_2$COO—(CH$_2$)$_2$N(Me)$_2$ | Me | H | Me | CH |
| 17 | H | H | (CH$_2$)$_3$NHCONH—(CH$_2$)$_2$N(Me)$_2$ | Me | H | Me | CH |
| 18 | H | H | (CH$_2$)$_2$CONH(CH$_2$)$_5$—CONH(CH$_2$)$_2$N(Me)$_2$ | Me | H | Me | CH |
| 19 | H | H | (CH$_2$)$_2$CONH(CH$_2$)$_2$NH—COCH$_2$S(CH$_2$)$_2$N(Me)$_2$ | Me | H | Me | CH |
| 20 | H | H | (CH$_2$)$_2$CONH(CH$_2$)$_5$NH—COCH$_2$S(CH$_2$)$_2$N(Me)$_2$ | Me | H | Me | CH |
| 21 | H | H | CH$_2$NHCOCH$_2$S—(CH$_2$)$_2$N(Me)$_2$ | Me | H | Me | CH |
| 22 | H | H | (CH$_2$)$_2$CONH(CH$_2$)$_2$N(piperazine)NH | Me | H | Me | CH |
| 23 | H | H | (CH$_2$)$_2$CONH(CH$_2$)$_2$N(piperazine)N—Me | Me | H | Me | CH |

TABLE 1-continued

Selected Embodiments of the Dyes of the Invention

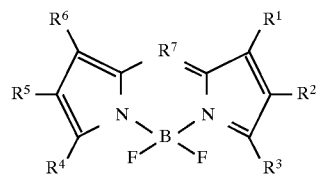

| Dye No. | $R^1$ | $R^2$ | $R^3$ | $R^4$ | $R^5$ | $R^6$ | $R^7$ |
|---|---|---|---|---|---|---|---|
| 24 | H | H | (CH$_2$)$_2$CON⟨NH⟩ | Me | H | Me | CH |
| 25 | H | H | (CH$_2$)$_2$CON⟨N—Me⟩ | Me | H | Me | CH |
| 26 | H | H | (CH$_2$)$_2$CONH(CH$_2$)$_2$N⟨imidazole⟩ | Me | H | Me | CH |
| 27 | H | H | (CH$_2$)$_2$CONH(CH$_2$)$_5$CONH—(CH$_2$)$_3$N(Me)(CH$_2$)$_3$NMe$_2$ | Me | H | Me | CH |
| 28 | H | H | (CH$_2$)$_2$CONH—(CH$_2$)$_2$NH$_2$ | C$_6$H$_5$ | H | C$_6$H$_5$ | CH |
| 29 | C$_6$H$_5$ | H | (CH$_2$)$_2$CONH—(CH$_2$)$_2$NHMe | H | H | H | CH |
| 30 | H | H | (CH$_2$)$_2$CONH—(CH$_2$)$_2$N(Me)$_2$ | C$_6$H$_5$ | H | C$_6$H$_5$ | CH |
| 31 | Me | Me | (CH$_2$)$_2$CONH—(CH$_2$)$_2$N(Me)$_2$ | p-(C$_6$H$_4$)OCH$_3$ | H | H | CH |
| 32 | Me | Me | (CH$_2$)$_2$CONH(CH$_2$)$_5$—CONH(CH$_2$)$_2$N(Me)$_2$ | p-(C$_6$H$_4$)OCH$_3$ | H | H | CH |
| 33 | H | H | (CH$_2$)$_2$CONH—(CH$_2$)$_2$N(Me)$_2$ | (C$_6$H$_4$)NH$_2$ | H | H | CH |
| 34 | H | H | (CH$_2$)$_2$CONH—(CH$_2$)$_2$N(Me)$_2$ | (C$_6$H$_4$)CHO | H | H | CH |
| 35 | H | H | (CH$_2$)$_2$CONH—(CH$_2$)$_2$N(Me)$_2$ | (C$_6$H$_4$)COOMe | H | H | CH |
| 36 | H | H | (CH$_2$)$_2$CONH—(CH$_2$)$_2$N(Me)$_2$ | (C$_6$H$_4$)N$_3$ | H | H | CH |
| 37 | H | H | (CH$_2$)$_2$CONH—(CH$_2$)$_2$N(Me)$_2$ | 1-NAPHTHYL | H | H | CH |
| 38 | H | H | (CH$_2$)$_2$CONH—(CH$_2$)$_2$N(Me)$_2$ | 2-FURANYL | H | H | CH |
| 39 | H | H | (CH$_2$)$_2$CONH—(CH$_2$)$_2$N(Me)$_2$ | 2-OXAZOLYL | H | H | CH |
| 40 | H | H | (CH$_2$)$_2$CONH—(CH$_2$)$_2$N(Me)$_2$ | 2-PYRROLYL | H | H | CH |
| 41 | H | H | (CH$_2$)$_2$CONH—(CH$_2$)$_2$NH$_2$ | 2-PYRROLYL | H | H | CH |
| 42 | H | H | (CH$_2$)$_2$CONH—(CH$_2$)$_2$N(Me)$_2$ | 2-THIENYL | H | H | CH |
| 43 | H | H | (CH$_2$)$_2$CONH—(CH$_2$)$_2$N(Me)$_2$ | 4-PYRIDYL | H | H | CH |
| 44 | H | H | (CH$_2$)$_2$CONH—(CH$_2$)$_2$N(Me)$_2$ | CH=CH(C$_6$H$_5$) | H | H | CH |
| 45 | H | H | (CH$_2$)$_2$CONH—(CH$_2$)$_2$N(Me)$_2$ | (CH=CH)$_2$(C$_6$H$_5$) | H | H | CH |
| 46 | (CH$_2$)$_2$SO$_2$—NH(CH$_2$)$_2$NH$_2$ | H | Me | Me | H | Me | CH |
| 47 | (CH$_2$)$_2$SO$_2$—NH(CH$_2$)$_2$N(CH$_3$)$_2$ | H | Me | Me | H | Me | CH |
| 48 | (CH$_2$)$_2$SO$_2$—NHNH$_2$ | H | Me | Me | H | Me | CH |
| 49 | (CH$_2$)$_2$NH$_2$ | H | Me | Me | H | Me | CH |
| 50 | H | Cl | (CH$_2$)$_2$CONH—(CH$_2$)$_2$N(Me)$_2$ | Me | Cl | Me | CH |
| 51 | H | Br | (CH$_2$)$_2$CONH— | Me | Br | Me | CH |

TABLE 1-continued

Selected Embodiments of the Dyes of the Invention

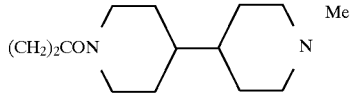

| Dye No. | R¹ | R² | R³ | R⁴ | R⁵ | R⁶ | R⁷ |
|---|---|---|---|---|---|---|---|
| 52 | H | I | (CH₂)₂N(Me)₂<br>(CH₂)₂CONH—<br>(CH₂)₂N(Me)₂ | Me | I | Me | CH |
| 53 | H | H | (CH₂)₂CONH—<br>(CH₂)₂N(Me)₂ | (CH₂)₂CONH—<br>(CH₂)₂NMe₂ | H | H | CH |
| 54 | Me | NHCOCH₂S—<br>(CH₂)₂N(Me)₂ | Me | Me | H | Me | CH |
| 55 | H | H | (CH₂)₂N(Me)₂ | Me | H | Me | CH |
| 56 | Me | H | Me | Me | H | Me | C(CH₂)₂NH₂ |
| 57 | C₆H₅ | H | C₆H₅ | C₆H₅ | H | C₆H₅ | C(CH₂)₂NMe₂ |
| 58 | Me | H | Me | Me | H | Me | C(CH₂)S—<br>(CH₂)₂N(Me)₂ |
| 59 | H | H | CH=CHCONH(CH₂)₂N(Me)₂ | H | H | H | CH |
| 60 | H | H | (CH₂)₂CON⟨piperidinyl-piperidine⟩ | Me | H | Me | CH |
| 61 | H | H | (CH₂)₂CON⟨cyclohexyl-piperidine⟩ | Me | H | Me | CH |
| 62 | H | H | (CH₂)₂CON⟨triazacycle HN...HN⟩ | Me | H | Me | CH |
| 63 | H | H | CH₂N(Me)₂ | CH₂N(Me)₂ | H | H | N |

TABLE 2

Additional Selected Embodiments of the Dyes of the Invention

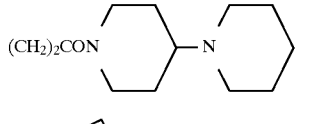

| Dye No. | Rₐ | R_b | R_c | R_d |
|---|---|---|---|---|
| 64 | (C₆H₄)OCH₂—COOMe | (C₆H₄)OCH₂CO—NH(CH₂)₂NMe₂ | H | OMe |
| 65 | (CH₂)₂CONH—(CH₂)₂NMe₂ | (CH₂)₂COOMe | H | H |
| 66 | (C₆H₄)OCH₂—COOMe | (C₆H₄)OCH₂CO—NH(CH₂)₂NMe₂ | H | H |
| 67 | (C₆H₄)NHCO(CH₂)₂— | (C₆H₄)NH₂ | H | H |

TABLE 2-continued

Additional Selected Embodiments of the Dyes of the Invention

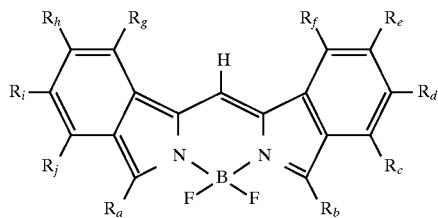

| | | | | |
|---|---|---|---|---|
| | CONH(CH$_2$)$_2$NMe$_2$ | | | |
| 68 | (C$_6$H$_4$)OCH$_2$CO—NH(CH$_2$)$_2$NMe$_2$ | (C$_6$H$_4$)OCH$_2$CONH—(CH$_2$)$_2$NMe$_2$ | H | H |
| 69 | (C$_6$H$_5$) | (C$_6$H$_5$) | H | OCH$_2$CONH—(CH$_2$)$_2$NMe$_2$ |
| 70 | 2-PYRIDYL | 2-PYRIDYL | H | H |
| 71 | 2-THIENYL | 2-THIENYL | H | H |
| 72 | 2-THIENYL-5-(CH$_2$)$_2$CONH—(CH$_2$)$_2$NMe$_2$ | 2-THIENYL-5-(CH$_2$)$_2$COOMe | H | H |
| 73 | (C$_6$H$_5$) | (C$_6$H$_5$) | H | H |
| 74 | (C$_6$H$_5$) | (C$_6$H$_5$) | —CH=CH—CH=CH— | |
| 75 | (C$_6$H$_4$)OCH$_2$COOMe | (C$_6$H$_4$)OCH$_2$CONH—(CH$_2$)$_2$NMe$_2$ | —CH=CH—CH=CH— | |

| Dye No. | R$_e$ | R$_f$ | R$_g$ | R$_h$ | R$_i$ | R$_j$ |
|---|---|---|---|---|---|---|
| 64 | H | H | H | H | OMe | H |
| 65 | H | H | H | H | H | H |
| 66 | H | H | H | H | H | H |
| 67 | H | H | H | H | H | H |
| 68 | H | H | H | H | H | H |
| 69 | H | H | H | H | OCH$_2$COOMe | H |
| 70 | OCH$_2$CONH—(CH$_2$)$_2$NMe$_2$ | H | H | OCH$_2$COOMe | H | H |
| 71 | OCH$_2$CONH—(CH$_2$)$_2$NMe$_2$ | H | H | OCH$_2$COOMe | H | H |
| 72 | H | H | H | H | H | H |
| 73 | —C(OCH$_2$CO$_2$Me)=CH—CH=CH— | CH— | —CH=CH— CH=C(OCH$_2$CONH—(CH$_2$)$_2$NMe$_2$)— | H | H | |
| 74 | OCH$_2$CONH—(CH$_2$)$_2$NMe$_2$ | H | H | H | H | H |
| 75 | H | H | H | H | —CH=CH—CH=CH— | |

Selected abbreviations used in Tables 1 and 2 are defined as follows:

Me=CH$_3$
Et=CH$_2$CH$_3$
Pr=CH$_2$CH$_2$CH$_3$
Bu=CH$_2$CH$_2$CH$_2$CH$_3$
(C$_6$H$_5$)=phenyl
(C$_6$H$_4$)=phenylene NAPHTHYL = 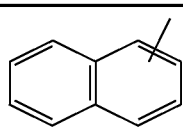

FURANYL = 

OXAZOLYL = 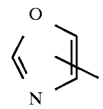

PYRROLYL = 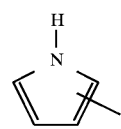

THIENYL = 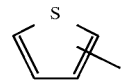

PYRIDYL = 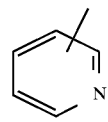

Synthesis

The dyes of the present invention are readily prepared using the methods described in U.S. Pat. No. 4,774,339 to Haugland, et al. (1988), U.S. Pat. No. 5,187,288 to Kang et al. (1993), U.S. Pat. No. 5,248,782 to Haugland, et al. (1993), U.S. Pat. No. 5,274,113 to Kang, et al. (1993), and U.S. Pat. No. 5,433,896 to Kang, et al. (1995) (all incorporated by reference). Methods for preparing aza-substituted dipyrromethene boron difluoride dyes are described in U.S. Pat. No. 5,446,157 to Morgan et al. (1995) (incorporated by reference). Those dyes of the present invention that feature fused aromatic rings at the positions $R^2$–$R^3$ or $R^4$–$R^5$ are prepared similarly from intermediates described by Müller et al., MONATSHEFTE FÜR CHEMIE 116,365 (1985). Specific methods for preparing the covalent linkage, LINK, are demonstrated in Examples 1–11.

Compounds wherein the LINK or CAP moiety incorporates a cyclic structure are prepared by reaction of a pre-formed reactive dye with an appropriate amine-containing intermediate, or by preparing amine-containing pyrroles prior to formation of the dye.

Use of the Dyes of the Invention to Stain Samples

The dyes of the invention are only partially protonated at neutral pH. By careful selection of the substituents on the dipyrromethene boron fluorophore, the spectral properties of the probe can be tuned over a wide range of the visible and near infra-red spectrum, making them especially useful for multicolor applications. Similarly, careful selection of substituents allow the pH selectivity of the dyes of the invention to be tuned for specific applications. For example, a dye having a CAP moiety that is less basic will be protonated by more acidic conditions, and therefore more selectively accumulate at locations having a lower pH.

The preferred dyes of the present invention are freely permeant to cell membranes, and typically selectively accumulate in acidic organelles. The staining characteristics are generally not reversed or are only partially reversed by subsequent treatment of the cells with additional weakly basic cell-permeant compounds. In some cases, the staining is preserved even after fixation and/or permeabilization of the cells.

The probes of the present invention are utilized by preparing a labeling solution containing one or more of the dyes of the present application, introducing the labeling solution into the sample containing or thought to contain acidic organelles, incubating the sample for a time sufficient to produce a detectable fluorescent staining pattern, and observing or analyzing the staining pattern in the sample. The sample may be a cell or cells that contain acidic organelles or the sample may contain isolated acidic organelles (i.e. not incorporated in a cell), or the sample may be two solutions separated by a semi-permeable membrane.

The degree of staining of acidic organelles is a reflection of the pH gradient present across the acidic organelles membrane at the time of staining, i.e., the degree of staining is indicative of whether or not the organelle is acidic at the time of staining. While the dyes of the present invention are typically used for staining the acidic organelles of live cells, the present invention is also useful for staining isolated (i.e. cell-free) acidic organelles, provided the organelles are not disrupted and a pH gradient still exists between the organelle and the medium in which it is suspended. While in general the presence of acidic organelles can be considered an indicator of cell viability, it is possible to render a cell non-viable, while still retaining acidic organelles in the sample.

Preparation of a Labeling Solution

The pure dyes generally have low solubility in water. Typically a stock solution is prepared by dissolving a known mass of the pure dye in an organic solvent. Preferred organic solvents are DMSO, DMF, N-methylpyrrolidone, acetone, acetonitrile, dioxane, tetrahydrofuran and other nonhydroxylic, completely water-miscible solvents. Alternatively, the dye is dispersed in a water immiscible solvent or oil, or is evaporated from an organic solvent leaving a thin film. The stock solutions should be protected from light at all times. The labeling solution is prepared by diluting an aliquot of the stock solution into an aqueous or partially aqueous buffer to the desired labeling concentration. In one embodiment of the invention, two or more dyes of the invention are present in the labeling solution, having similar or distinct spectral properties.

In general the amount of dye added in the labeling solution is the minimum amount required to yield detectable staining of the acidic organelles present in the sample within a reasonable time, with minimal background fluorescence or staining of other organelles or cellular structures. The amount of dye required for staining eukaryotic cells depends on the sensitivity required for staining the intracellular acidic organelles, the number of cells present, the permeability of the cell membrane to the dye, and the time required for the probe to localize to the organelles. The required concentration for the labeling solution is determined by systematic variation in labeling concentration until a satisfactory fluorescent labeling is accomplished. Typically, the amount of dye required for staining animal cells is 20 to 400 nM, preferably below 100 nM.

Low concentrations of dye require longer incubation times for equivalent fluorescent brightness to be reached. Typically cells incubated in 35 nM labeling solution require about 2.5 hours to reach an arbitrary level of fluorescent staining that is reached in about 40 minutes using a 75 nM labeling solution. For those embodiments where the acidic organelles to be stained are vacuoles present in plant cells, yeast or other fungal cells, a higher concentration of dye is used, due to the lower permeability of the yeast cell membrane. Typically, when staining fungal cells, a dye concentration of 10 $\mu$M is satisfactory to give good vacuolar staining.

Staining concentrations less than about 100 nM give good staining of acidic organelles in live animal cells. At higher concentrations of stain, background fluorescence increase in live cells, but resolution of acidic organelles after fixation is improved. Staining of isolated (cell-free) acidic organelles typically requires lower concentrations of dye.

The exact concentration of stain to be used is dependent upon the experimental conditions and the desired results and optimization of experimental conditions is required to determine the best concentration of stain to be used in a given application.

Sample Types

The sample optionally comprises cell-free acidic organelles or cells that contain acidic organelles. Any cells that contain acidic organelles can be used, including but not limited to, fresh or cultured cells, cell lines, cells in biological fluids, cells in tissue or biopsy, yeast cells, plant cells and sperm cells. Where the sample contains cells, the cells are optionally abnormal cells, such as tumor cells or other cancer cells, where the abnormal cells are present in vitro or in vivo. Acidic organelles of interest that are stained using the present method of staining include, but are not limited to, lysosomes, phagovacuoles, endosomes, yeast vacuoles and acrosomes. In one embodiment of the invention, the staining method is used to stain all lysosomal compartments in the sample. Typically, the acidic organelles that are stained are lysosomes or acrosomes. More typically, the acidic organelles that are stained are lysosomes.

Most plant and fungal cells (including the unicellular fungi and yeast) contain one or more very large, fluid-filled vesicles called vacuoles. In yeast, the vacuoles typically occupy more than 70% of the cell volume. Yeast vacuoles are related to lysosomes of animal cells, and contain a variety of hydrolytic enzymes with acidic pH in the lumen.

Mature sperm cells, spermatozoa, are relatively simple cells, containing only a cell membrane, a compact nucleus and a vesicle, called an acrosome. The acrosome is derived from a Golgi body and is located at the leading tip of the sperm cell. The acrosome is an acidic compartment containing enzymes that aid in the penetration of the protective layers surrounding egg, initiating the egg activation step (the first step in the fertilization process). Therefore, acrosomes play a very important role in egg fertilization.

The method of the present invention is useful for the staining and monitoring of sperm acrosomes. Only healthy sperm cells with acidic acrosomes are stained. The resulting stained sperm cells can then be sorted using flow cytometry or another fluorescence-sensitive device in order to improve fertilization rate, or to conduct research.

Staining the Sample

The sample is typically stained by passive means, that is the labeling solution is combined with the sample being analyzed. The dyes of the present invention are introduced into the sample organelles by incubation of the sample in the labeling solution. Where the sample contains a cell or cells, the cells are similarly stained by incubation of the cell or cells in the labeling solution. Alternatively, the sample is stained by direct uptake of the dye from a thin film of the dye itself. Any other method of introducing the dye into the sample cell, such as microinjection of a labeling solution, can be used to accelerate introduction of the dye into the cellular cytoplasm. Typically the dye will be introduced into the sample cell by incubation in the labeling solution, or by microinjection. Preferably the dye is introduced to the sample by incubation in the labeling solution. Microinjection of dye solution is used when labeling of the acidic organelles in a single cell is desired, within a colony of other sample cells.

A number of reagents and conditions are known to affect the pH gradient of acidic organelles, and therefore the staining of the dyes of the invention, including but not limited to nutrients (for example carbohydrates such as glucose) and selected drugs.

The dyes of the present invention are generally non-toxic to living cells and acidic organelles. Sample cells have been incubated in 75 nM dye solution for 36 hours without observable ill effects. Stained cells have been observed to undergo cell division, producing daughter cells that also possess stained acidic organelles.

Preparation for Observation

Optionally, the cells or isolated acidic organelles are washed to improve the results of the staining procedure. Washing the sample cell or cells after incubation in the labeling solution, or optionally after fixation or permeabilization, greatly improves the visualization of the acidic organelles. This is largely due to the decrease in non-specific background fluorescence after washing. Satisfactory visualization of acidic organelles is possible without washing by using low labeling concentrations (for example <50 nM).

The sample can be observed immediately after staining of acidic organelles is evident. After staining, the cells or isolated acidic organelles in a sample are optionally fixed. Selected embodiments of the dyes described above are well retained in cells, and sample cells stained with these dyes retain considerable fluorescent staining after fixation. A number of fixatives and fixation conditions are suitable for practicing this invention. Useful fixatives include, but are not limited to, formaldehyde, paraformaldehyde, formalin, glutaraldehyde, cold methanol and 3:1 methanol acetic acid. Typically, cell fixation is accomplished by incubating the stained cells in a 3.7% solution of paraformaldehyde for about 15–30 minutes. Fixation is typically used to preserve cellular morphology and to reduce biohazards when working with pathogenic samples.

Fixation is optionally followed or accompanied by permeabilization, such as with acetone, ethanol, DMSO or various detergents. Permeabilization is utilized to allow bulky additional detection reagents to enter the cellular space that would ordinarily be impermeant to an intact cellular membrane. A large variety of fixatives, fixation conditions, and permeabilization agents are known in the art, and other methods of fixing or permeabilizing sample cells in conjunction with the stains of the present invention will be obvious to one of ordinary skill.

Additional Detection Reagents

The use of the acidic organelle stains of the present invention is optionally combined with the use of an additional detection reagent. An additional detection reagent is a reagent that produces a detectable response due to the presence of a specific cell component, intracellular substance, or cellular condition. One or more additional detection reagents may be used in conjunction with the stains of the present invention, before or after fixation and/or permeabilization. The additional detection reagent may be used to stain the entire cell, or a cellular substructure. The fluorescent signal of the acidic organelle stains of the present invention and the detectable response of the additional detection reagent may be observed simultaneously or sequentially. The observation of acidic organellar staining and a detectable response that are spatially coincident indicate that the additional detection reagent is associated with the acidic organelles. A variety of measurements can be made within acidic organelles in this manner, even when the additional detection reagent does not itself localize selectively within the acidic organelles.

One class of appropriate additional detection reagents are fluorescent nucleic acid stains. A wide variety of appropriate nucleic acid stains are known in the art, including but not limited to, Thiazole Orange, ethidium homodimer, propidium iodide, Hoechst 33258 (Example 21), and DAPI. Additional useful nucleic acid stains are described in the international applications WO 93/06482, DIMERS OF UNSYMMETRICAL CYANINE DYES (published Apr. 1, 1993); U.S. Pat. No. 5,436,134 to Haugland et al., 1995; U.S. Pat. No. 5,321,130 to Yue et al, 1994; U.S. Pat. No. 5,410,030 to Yue et al., 1995; or U.S. Pat. No. 5,437,980 to Haugland et al., 1995. The use of an appropriate nucleic acid stain in conjunction with the dyes of the present invention can be selected to allow simultaneous observation of acidic organelles, nuclear DNA, cellular RNA and/or mitochondrial DNA. Of particular utility is an additional detection reagent that is a cell-permeant nucleic acid stain, such as those described in U.S. Pat. No. 5,436,134, allowing simultaneous visualization of acidic organelles and the cell nucleus.

Other appropriate additional detection reagents include selected fluorescent metal ion indicators described in U.S. Pat. No. 5,453,517 to Kuhn et al. (1995), or U.S. Pat. No. 5,405,975 to Kuhn et al. (1995).

In another embodiment of the invention, an appropriate additional detection reagent is any probe that selectively stains a cellular organelle such as the cell membrane, nucleus, Golgi apparatus, mitochondrion, endoplasmic reticulum, or is a second acidic organelle probe.

Specific examples of additional detection reagents include mitochondria-targeted stains, such as Rhodamine 123. Additional fluorescent stains specific for mitochondria are described in U.S. Pat. No. 5,459,268 to Haugland et al. (1995) (hereby incorporated by reference). The above mitochondrial stains accumulate in mitochondria, and are fixable therein, allowing simultaneous visualization of both mitochondria and acidic organelles in fixed and permeabilized cells.

In one embodiment, the additional detection reagent comprises: a) one member of a specific binding pair or a series of specific binding pairs, and b) a means for producing a detectable response. A specific binding pair member can be a ligand or a receptor. As used in this document, the term ligand means any organic compound for which a receptor naturally exists or can be prepared. A receptor is any compound or composition capable or recognizing a spatial or polar organization of a molecule, e.g. epitopic or determinant site. Ligands for which naturally occurring receptors exist include natural and synthetic peptides and proteins, including avidin and streptavidin, antibodies, enzymes, and hormones; nucleotides and natural or synthetic oligonucleotides; lipids; polysaccharides and carbohydrates; lectins; and a variety of drugs, including therapeutic drugs and drugs of abuse and pesticides. Ligands and receptors are complementary members of a specific binding pair, each specific binding pair member having an area on the surface or in a cavity which specifically binds to and is complementary with a particular spatial and polar organization of the other.

The additional detection reagent may be used in conjunction with enzyme conjugates to localize cellular receptors; to localize hybridization probes; or to probe cells and tissues that do not express the enzyme, for example, by enzyme-linked immunosorbent assay (ELISA), or enzyme-mediated histochemistry or cytochemistry, or other enzyme-mediated techniques. Enzyme-mediated techniques take advantage of the attraction between specific binding pairs to detect a variety of analytes. In one embodiment, the additional detection reaction comprises an enzyme substrate to produces a fluorescent precipitate in the presence of the appropriate enzyme, as described in U.S. Pat. No. 5,316,906 to Haugland et al. (1994) and U.S. Pat. No. 5,443,986 to Haugland et al. (1995).

In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a "complementary conjugate". Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

The additional detection reagent also incorporates a means for producing a detectable response. A detectable response means a change in, or occurrence of, a parameter in a test system which is capable of being perceived, either by direct observation or instrumentally, and which is a function of the presence of a specifically targeted member of a specific binding pair in a cell sample. Such detectable responses include the change in, or appearance of, color, fluorescence, reflectance, pH, chemiluminescence, infrared emission, or the deposition of an electron-rich substrate. Appropriate labels to provide a detectable response include, but are not limited to, a visible or fluorescent dye, an enzyme substrate which produces a visible or fluorescent precipitate upon enzyme action (for example, the action of horseradish peroxidase upon diaminobenzidine), visible or fluorescent labeled latex microparticles, or a signal that is released by the action of light upon the reagent (e.g. a caged fluorophore that is activated by photolysis, or the action of light upon diaminobenzidine).

Observation

At any time after or during staining, the sample is illuminated with a wavelength of light that results in a detectable fluorescence response, and subsequently observed with a means for detecting the detectable response of fluorescent labeled acidic organelles, if present. In one embodiment of the invention, the fluorescently labeled organelles are observed after the cell or cells have additionally been fixed and/or permeabilized. Observation is accomplished using visible light microscopy, or alternatively, observation of the sample comprises illuminating the stained sample with a wavelength of light appropriate to generate a fluorescent response, and visually examining the sample by use of a microscope, or confocal microscope.

The sample is optionally illuminated at a wavelength specific for optimal excitation of a single dye present in the sample. Where the sample contains more than one dye, or contains an additional detection reagent, illumination occurs at a wavelength that generates a detectable fluorescence response in each dye or additional detection reagent, where said dyes and detection reagents possess overlapping excitation maxima.

Typically, the dyes of the invention typically possess a strong absorbance at visible wavelengths, typically at greater than 450 nm, preferably at greater than 600 nm, yet more preferably at greater than 650 nm. The preferred dyes of the invention exhibit an extinction coefficient greater than 50,000 $cm^{-1}M^{-1}$, preferably at greater than 80,000 $cm^{-1}M^{-1}$. The dyes of the invention typically possess quantum yields of fluorescence emission that are greater than 0.3, preferably greater than 0.7.

Optionally, the sample is observed using instrumentation. For example, where the sample contains a cell or cells, observation of the sample is accomplished by illuminating the stained cell or cells with a wavelength of light appropriate to generate a fluorescent response, and electronically detecting and optionally quantifying the fluorescent emission of the stained acidic organelles using an appropriate instrument, such as a fluorometer, fluorescent microplate reader, or a flow cytometer.

The observation of the fluorescent response of the sample optionally includes selecting or sorting the acidic organelles based upon their fluorescent response. Typically the sample comprises cells having stained acidic organelles, and the cells of the sample are sorted based upon the staining of the individual cells. The step of sorting is typically accomplished using a flow cytometer or a fluorescence microscope.

Photodynamic Therapy

The use of simple dipyrrometheneborondifluoride dyes as sensitizing agents to enhance photodynamic therapy (PDT) has been described by Boyer (U.S. Pat. No. 5,189,029; incorporated by reference) and Morgan (U.S. Pat. No. 5,446, 157; incorporated by reference). Photodynamic therapy refers to the process wherein illumination is utilized to destroy cells, typically abnormal cells, that have previously been labeled with a dye. Several references, including Geze, et al. (PHOTOCHEM. PHOTOBIOL. 20, 23–35 (1993); incorporated by reference) and Berg et al. (INT. J. CANCER 59, 814–822 (1994); incorporated by reference) have previously indicated that the photolysis of dyes that are localized to lysosomes destroys tumor cells. Furthermore, the lysosomes of tumor cells are generally considered to have a lower pH than normal lysosomes ("Molecular Aspects of Anticancer Drug Action", Neidel and Waring, Eds., Macmillan, London; pp 233–286 (1983), incorporated by reference). Selective uptake of PDT dyes into tumor cells in preference to normal cells is an important property allows selective photodestruction of abnormal cells in the course of PDT treatment, while minimizing the destruction of normal cells.

The method of the current invention has utility for photodynamic therapy, as described above, as the greater acidity of lysosomes in tumor cells, will result in greater uptake of the acidotropic dyes in tumor cells. Photolysis of the stained cells will then result in destruction of the target cells. Although cells and tissues stained according to the present method are potential PDT targets, preferably the dipyrrometheneborondifluoride dyes used for PDT targeting of cells are those that absorb beyond 600 nm, more preferably those that absorb beyond 650 nm, due to the enhanced penetration of light through tissue at these wavelengths. Particularly preferred are the dyes of the invention having fused benzo substituents, as described in U.S. Pat. No. 5,433,896 to Kang et al. (1995) that are further substituted by a LINK-CAP moiety. Additional preferred dyes of the invention for PDT are those having bromine or iodine substituents.

Preferred dye concentrations for labeling cells for PDT are those concentrations that have been determined to produce the greatest selective uptake of dye into abnormal cells without detriment to normal cells, such that photolytic activity is maintained in the abnormal cells. As described above, submicromolar concentrations of dye are effective in staining acidic organelles of live cells. The dyes are applied to cells for PDT by means well understood in the art, including local or systemic injection, topical application, incorporation into liposomes or other means. Dye uptake into cells is by passive diffusion or receptor-mediated uptake. Selective accumulation in lysosomes is facilitated by the pH gradient that favors uptake into the more acidic organelles. Photolysis is performed with any excitation source that is capable of producing light that can be absorbed by the dye, including lasers and light sources that produce infrared irradiation. This light may be delivered either directly to the cells that contain the dye, or delivered indirectly such as through an optical fiber. Fluorescence properties of the dye can be used to guide and determine which cells are to be irradiated.

The examples below are given so as to illustrate the practice of this invention. They are not intended to limit or define the entire scope of this invention.

EXAMPLES

Example 1

Preparation of Dye 1

The following compound is prepared:

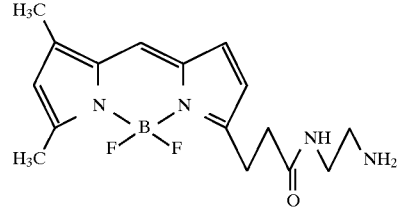

To a solution of 1.2 g of ethylenediamine (20.6 mmoles) in 10 mL of dichloromethane is dropwise added 100 mg of 4,4-difluoro-5,7-dimethyl-4-bora-3a,4a-diaza-s-indacene-3-propionic acid, succinimidyl ester (0.25 mmoles) in 10 mL of dichloromethane at 0° C. under vigorous stirring. The mixture is warmed up to room temperature, and continuously stirred for 2 hours. The resulted solution is poured into water, and extracted with chloroform. The chloroform layer is dried over anhydrous sodium sulfate, and evaporated in vacuo to afford orange solid. The solid is purified on a SEPHADEX LH-20 resin column using 1:1 water/methanol as an eluant. $R_f$=0.58 in 70:25:5 chloroform/methanol/acetic acid. $^1$H-NMR (in $CD_3OD$): 7.46 (s, 1H); 7.00 (s, 1H); 6.32 (s, 1H); 6.21 (s, 1H); 3.43 (t, 2H); 3.24 (t, 2H); 3.05 (t, 2H); 2.67 (t, 2H); 2.51 (s, 3H) and 2.28 ppm (s, 3H).

Example 2

Preparation of Dye 3

The following compound is prepared:

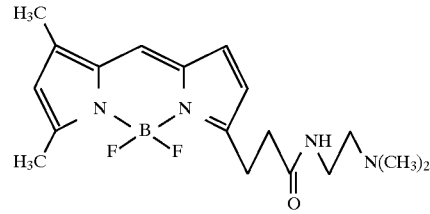

To a solution of 100 mg of 4,4-difluoro-5,7-dimethyl-4-bora-3a,4a-diaza-s-indacene-3-propionic acid, succinimidyl ester (0.25 mmoles) in 10 mL of dichloromethane is added dropwise 26.4 mg of N,N-dimethylethylenediamine (0.3 mmoles) in 10 mL of dichloromethane at 0° C. under stirring. The mixture is warmed to room temperature, and continuously stirred for 6 hours. The resulting solution is diluted using chloroform, and washed with water. The chloroform layer is dried over anhydrous sodium sulfate, and evaporated in vacuo to afford orange solid. The solid is purified on a silica gel column using 1:1 ethyl acetate/acetonitrile as an eluant. $R_f$=0.33 in 3:1 chloroform/methanol. $^1$HNMR (in $CD_3OD$): 7.43 (s, 1H); 7.00 (s, 1H); 6.31 (s, 1H); 6.19 (s, 1H); 3.37 (t, 2H); 3.21 (t, 2H); 2.60 (t, 2H); 2.50 (t, 2H); 2.41 (s, 6H); 2.39 (s, 3H) and 2.27 ppm (s, 3H).

Example 3
Preparation of Dye 21
The following compound is prepared:

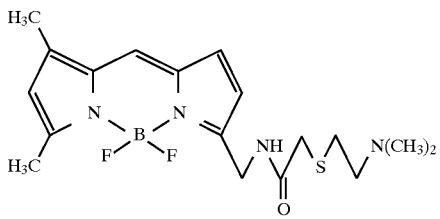

To a solution of 10 mg of 2-dimethylaminoethanethiol hydrochloride and 7 mg of sodium acetate in 1 mL of methanol is added 20 mg of 4,4-difluoro-5,7-dimethyl-3-iodoacetamidomethyl-4-bora-3a,4a-diaza-s-indacene and the mixture is stirred at room temperature in the dark for 3 hours. The reaction mixture is diluted with chloroform (25 mL), washed with water, dried over anhydrous $Na_2SO_4$ and concentrated to give a crude product. The crude product is then purified by column chromatography on silica gel using 2% methanol in chloroform as eluant.

Example 4
Preparation of Dye 24
The following compound is prepared:

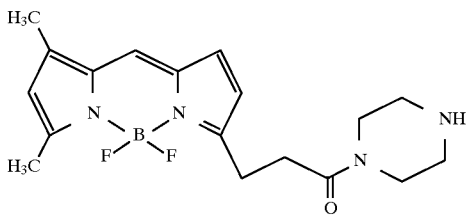

To a solution of piperazine (0.5 mmoles) in 10 mL of dichloromethane is added dropwise 100 mg of 4,4-difluoro-5,7-dimethyl-4-bora-3a,4a-diaza-s-indacene-3-propionic acid, succinimidyl ester (0.25 mmols) in 10 mL of dichloromethane at 0° C. with vigorous stirring. The reaction mixture is then warmed to room temperature and stirred an additional 2 hours. The resulting solution is poured into water, and extracted with chloroform. The organic layer is dried over anhydrous $Na_2SO_4$ and evaporated under reduced pressure to afford an orange solid. The solid is purified on a SEPHADEX LH-20 resin column using 9:1 methanol-water as an eluant.

Example 5
Preparation of Dye 26
The following compound is prepared:

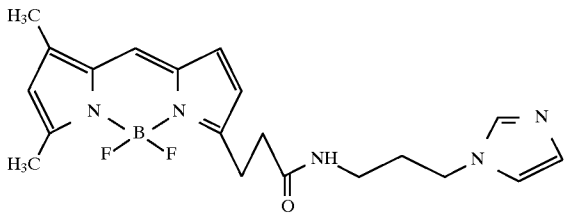

To a solution of 100 mg of 4,4-difluoro-5,7-dimethyl-4-bora-3a,4a-diaza-s-indacene-3-propionic acid, succinimidyl ester (0.25 mmoles) in 10 mL of dichloromethane is added dropwise 43.2 mg of 3-aminopropyl imidazole (0.3 mmoles) in 10 mL of dichloromethane at 0° C. with stirring. The reaction mixture is warmed to room temperature, and stirred an additional 6 hours. The resulting solution is then diluted with chloroform and washed with water. The organic layer is dried over anhydrous $Na_2SO_4$ and evaporated under reduced pressure to afford an orange solid. The solid is purified on a silica gel column using 1:1 ethyl acetate/acetonitrile as eluant.

Example 6
Preparation of Dye 28
The following compound is prepared:

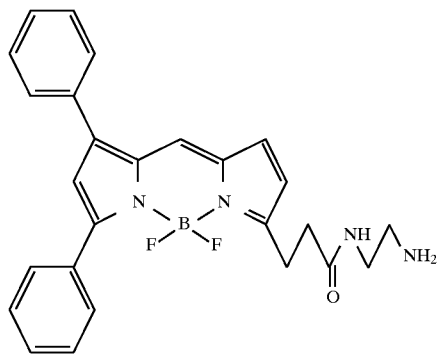

To a solution of 1.2 g ethylenediamine (20.6 mmoles) in 10 mL of dichloromethane is dropwise added 100 mg of 4,4-difluoro-5,7-diphenyl-4-bora-3a,4a-diaza-s-indacene-3-propionic acid, succinimidyl ester (0.20 mmoles) at 0° C. under vigorous stirring. The mixture is warmed up to room temperature, and continuously stirred for 2 hours. The resulted solution is poured into water, and extracted with chloroform. The chloroform layer is dried over anhydrous sodium sulfate, and evaporated in vacuo to afford orange solid. The solid is purified on a silica gel column using 95:5 ethyl acetate/chloroform as eluant. $R_f$=0.58 in 95:5 ethyl acetate/chloroform. $^1$HNMR (in $CDCl_3$): 7.89 (d, 2H); 7.47 (m, 7H); 7.19 (s, 1H); 6.92 (dd, 1H); 6.62 (s, 1H); 6.36 (dd, 1H); 3.33 (t, 2H); 3.22 (t, 2H); 2.84 and 2.61 ppm (m, 4H).

Example 7
Preparation of Dye 30
The following compound is prepared:

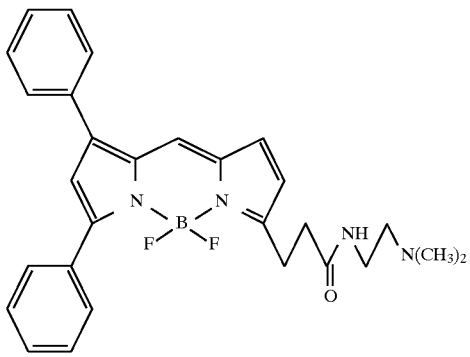

To a solution of 100 mg of 4,4-difluoro-5,7-diphenyl-4-boro-3a,4a-diaza-s-indacene-3-propionic acid, succinimidyl ester (0.25 mmoles) in 10 mL of dichloromethane is dropwise added 22.0 mg of N,N-dimethylethylenediamine (0.25 mmoles) in 10 mL of dichloromethane at 0° C. under stirring. The mixture is warmed up to room temperature, and continuously stirred for 6 hours. The resulted solution is

Example 8
Preparation of Dye 40
The following compound is prepared:

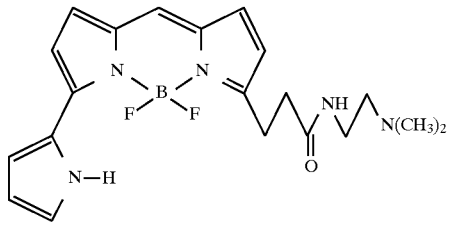

To a solution of 100 mg of 4,4-difluoro-5-(2-pyrrolyl)-4-bora-3a,4a-diaza-s-indacene-3-propionic acid, succinimidyl ester (0.23 mmoles) in 10 mL of dichloromethane is dropwise added 22.0 mg of N,N-dimethylethylenediamine (0.25 mmoles) in 10 mL of dichloromethane at 0° C. under stirring. The mixture is warmed to room temperature, and continuously stirred for 6 hours. The resulted solution is diluted using chloroform, and washed with water. The chloroform layer is dried over anhydrous sodium sulfate, and evaporated in vacuo to afford red solid. The solid is purified on a silica gel column using 9:1 chloroform/ethyl acetate as the eluant. $R_f$=0.39 in 3:1 chloroform/methanol. $^1$HNMR (in CDCl$_3$): 7.17 (s, 1H); 7.03 (dd, 1H); 6.97 (s, 2H); 6.86 (dd, 1H); 6.85 (dd, 1H); 6.48 (s, 1H); 6.37 (s, 1H); 6.31 (dd, 1H); 3.38 (t, 2H); 3.28 (t, 2H); 2.64 (t, 2H); 2.51 (t, 2H) and 2.29 ppm (s, 6H).

Example 9
Preparation of Dye 51
The following compound is prepared:

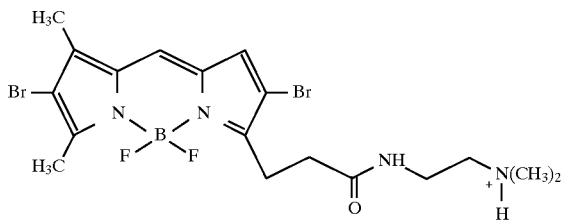

To a solution of 50 mg of 4,4-difluoro-5,7-dimethyl-4-bora-3a,4a-diaza-s-indacene-3-propionic acid in 10 mL of 1,2-dichloroethane is added 60 mg of N-bromosuccinimide. After the reaction mixture is heated at reflux for 1 hour, it is cooled to room temperature and washed with water (2×10 mL). The separated organic layer is dried over anhydrous Na$_2$SO$_4$. After concentration of the solvent under reduced pressure, the crude product of 2,6-dibromo-4,4-difluoro-5,7-dimethyl-4-bora-3a,4a-diaza-s-indacene-3-propionic acid is obtained. The crude product is purified by silica gel column chromatography using 3% methanol in chloroform as eluant to give 57 mg of the pure product.

A sample of 20 mg of the acid is converted to a reactive succinimidyl ester as follows: To a solution of 20 mg of the above acid in 10 mL of ethyl acetate is added 7 mg of N-hydroxysuccinimide, followed by addition of 10 mg of N,N-dicyclohexylcarbodiimide and the mixture is stirred at room temperature for 3 hours. The reaction mixture is concentrated under reduced pressure and is subjected to silica gel column using chloroform as eluant to give 20 mg of the reactive succinimidyl ester derivative.

The above succinimidyl ester (20 mg) is added to a solution of 30 µL of N,N-dimethylethylenediamine in 5 mL of dichloromethane. After the mixture is stirred at room temperature for 1 hour, it was subjected to silica gel column chromatography using 10% methanol in chloroform. The desired fractions from the column are combined and treated with 200 µL of 4M HCl solution. The resulting solution is concentrated under reduced pressure and the residue is applied to a short SEPHADEX LH-20 resin column and eluted with water. The desired fractions are combined and lyophilized to give the desired product as the hydrochloride salt.

Example 10
Preparation of Dye 52
The following compound is prepared:

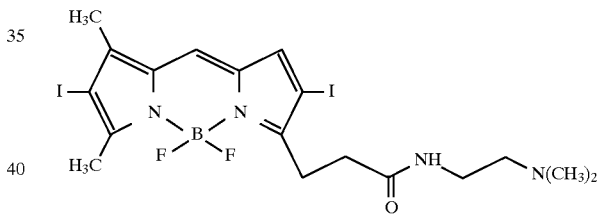

To a solution of 20 mg of 4,4-difluoro-4-bora-3a,4a-diaza-s-indacene-3,5-dipropionic acid in 0.5 mL of DMF is added 50 mg of O-(N-succinimidyl)-N,N,N',N'-tetramethyluronium tetrafluoroborate and the mixture is stirred at room temperature for 1 hour. This activated succinimidyl ester solution is added into a solution of 30 µL of N,N-dimethylethylenediamine in 5 mL of dichloromethane. After stirring at room temperature for 1 hour, it is subjected to silica gel column chromatography using 15% methanol in chloroform. The desired fractions from the column are combined and treated with 300 µL of 4M HCl solution. The resulting solution is concentrated under reduced pressure and the resulting residue is applied to a SEPHADEX LH-20 resin column and eluted with water. After lyophilization of the desired combined fractions, the desired product is obtained.

Example 11
Preparation of Dye 53
The following compound is prepared:

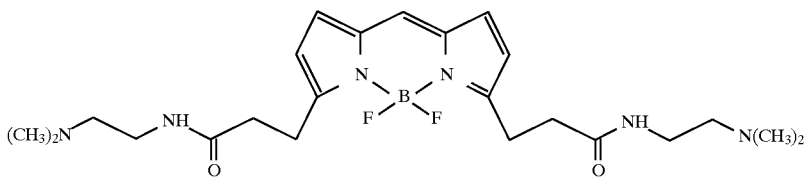

To a solution of 20 mg of 4,4-difluoro-4-bora-3a,4a-diaza-s-indacene-3,5-dipropionic acid in 0.5 mL of DMF is added 50 mg of O-(N-succinimidyl)-N,N,N',N'-tetramethyluronium tetrafluoroborate and the mixture is stirred at room temperature for 1 hour. This activated succinimidyl ester solution is added to a solution of 30 μL of N,N-dimethylethylenediamine in 5 mL of dichloromethane. After stirring at room temperature for 1 hour, the reaction mixture is purified by silica gel column chromatography using 15% methanol in chloroform as eluant. The desired fractions are combined, and treated with 300 μL of 4M HCl solution. The resulting solution is concentrated under reduced pressure and the resulting residue is subjected to SEPHADEX LH-20 resin column and eluted with water. After lyophilization, the desired product is obtained.

Example 12
Preparation of Dye 54
The following compound is prepared:

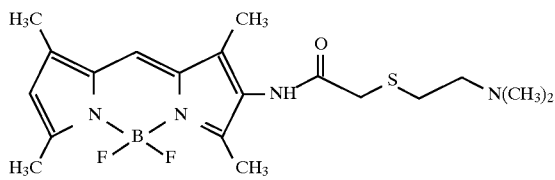

Dye 54 is prepared analogously to Dye 21 above (Example 3), excepting that 4,4-difluoro-1,3,5,7-tetramethyl-2-iodoacetamido-4-bora-3a,4a-diaza-s-indacene is used in place of 4,4-difluoro-5,7-dimethyl-3-iodoacetamidomethyl-4-bora-3a,4a-diaza-s-indacene.

Example 13
Preparation of Dye 55
The following compound is prepared:

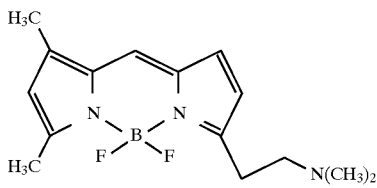

To a solution of 100 mg of 3,5-dimethylpyrrole-2-carboxaldehyde and 110 mg of 2-(2-dimethylaminoethyl) pyrrole in 20 mL of dichloromethane is added 75 μL of POCl$_3$ and the mixture is stirred at room temperature for 3 hours. To the reaction mixture is added 700 μL of triethylamine, followed by addition of 400 μL of BF$_3$.Et$_2$O. After stirring at room temperature for an additional 5 hours, the reaction mixture is washed with water, dried over anhydrous Na$_2$SO$_4$ and concentrated to give a crude product. The crude product is purified by column chromatography on silica gel using 1% methanol in chloroform as eluant.

Example 14
Preparation of Dye 58
The following compound is prepared:

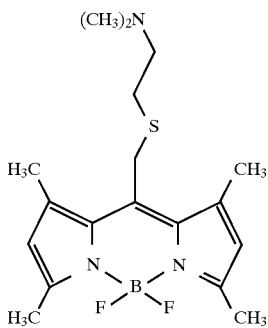

To a solution of 10 mg of 4,4-difluoro-8-bromomethyl-1,3,5,7-tetramethyl-4-bora-3a,4a-diaza-s-indacene in 1 mL of dry CH$_3$CN is added 2-dimethylethanethiol. After stirring at room temperature for 15 hours, the reaction mixture is diluted with 30 mL of chloroform and washed with 5% sodium bicarbonate solution (2×30 mL). The separated organic layer is dried over anhydrous Na$_2$SO$_4$ and concentrated to give a crude product. The crude product is purified by column chromatography on silica gel using 10% methanol in chloroform to give the desired product.

Example 15
Preparation of Dye 60
The following compound is prepared:

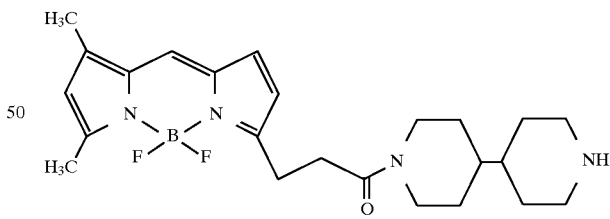

To a solution of 602 mg of 4,4'-bipiperidine dihydrochloride (2.5 mmoles) in 10 mL of pyridine is added dropwise 100 mg of 4,4-difluoro-5,7-dimethyl-4-bora-3a,4a-diaza-s-indacene-3-propionic acid, succinimidyl ester (0.25 mmoles) in 10 mL of dichloromethane at 0° C. with vigorous stirring. The reaction mixture is then warmed to room temperature and stirred an additional 2 hours. The resulting solution is poured into water and extracted with chloroform. The organic layer is dried over anhydrous Na$_2$SO$_4$, and dried under reduced pressure to afford an orange solid. The solid product is then purified on a SEPHADEX LH-20 column using 9:1 methanol water as eluant.

Example 16
Preparation of Dye 61
The following compound is prepared:

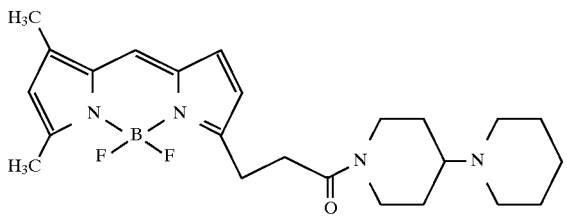

To a solution of 100 mg of 4,4-difluoro-5,7-dimethyl-4-bora-3a,4a-diaza-s-indacene-3-propionic acid, succinimidyl ester (0.25 mmoles) in 10 mL of dichloromethane is added 50.4 mg of 4-piperidinopiperidine (0.3 mmoles) in 10 mL dichloromethane at 0° C. with stirring. The reaction mixture is then warmed to room temperature and stirred an additional 6 hours. The resulting solution is diluted with chloroform and washed with water. The organic layer is dried over anhydrous $Na_2SO_4$, and dried under reduced pressure to afford an orange solid. The solid product is then purified on a silica gel column using 9:1 methanol water as eluant.

Example 17
Preparation of Dye 62
The following compound is prepared:

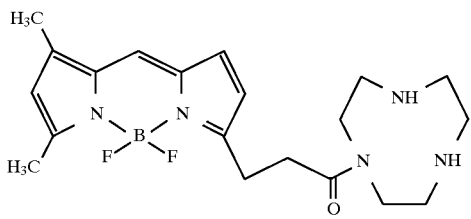

To a solution of 6.5 g of 1,4,7-triazacyclononane in 10 mL of pyridine is added dropwise 100 mg of 4,4-difluoro-5,7-dimethyl-4-bora-3a,4a-diaza-s-indacene-3-propionic acid, succinimidyl ester (0.25 mmoles) in 10 mL of dichloromethane at 0° C. with vigorous stirring. The reaction mixture is then warmed to room temperature and stirred an additional 2 hours. The resulting solution is poured into water and extracted with chloroform. The organic layer is dried over anhydrous $Na_2SO_4$, and dried under reduced pressure to afford an orange solid. The solid product is then purified on a SEPHADEX LH-20 column using water as eluant.

Example 18
Preparation of Dye 63
The following compound is prepared:

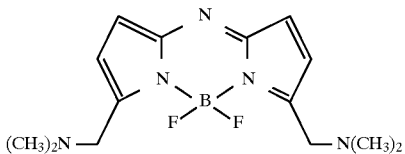

Two equivalents of 4-cyano-1-(dimethylamino)butan-2-one are condensed with hydroxylamine to give 8-azapyrromethene. This intermediate is then treated with $BF_3.Et_2O$ in dichloromethane to give the desired aza-dipyrromethenboron difluoride dye.

Example 19
Preparation of cell culture
A calf pulmonary arterial endothelium (CPAE) cell line is obtained from American Type Culture Collection Co., Rockville Md. The cells are maintained in a humidified atmosphere of 5% $CO_2$ in Dulbecco's modified Eagle's medium (DMEM) supplemented with 10% calf serum, 50 μg/mL gentamicin, 300 μg/mL L-glutamime and 10 mM HEPES pH 7.4. Cells are subcultured every 2–3 days by trypsinization using 0.05% trypsin and 0.02% EDTA in a calcium- and magnesium-free saline solution (Gibco BRL, Gaithersburg, Md.). To obtain well-spread single cells, cells are plated at a low density onto No. 1½ (18×18 mm) cover glasses in 100 mm culture dishes, and used 24–48 hours after plating.

Example 20
Preparation of labeling solution
The desired dye of the invention is separately dissolved in DMSO to prepare a 1 mM dye stock solution. The stock solution is kept sealed in small aliquots, at -20° C. The stock solution is kept frozen at all times until use, and exposure to light is minimized. One aliquot of dye stock is taken from the freezer immediately before an experiment and thawed completely at room temperature. The labeling solution is then prepared by adding the dye stock solution to fresh culture medium in an amount sufficient to make final dye concentrations of 50 and 200 nM, respectively.

Example 21
Labeling of lysosomes and acidic organelles in live animal cells
Cells prepared according to Example 19 are transferred to the labeling solution containing Dye 40 (Example 8), prepared according to Example 20, and incubated at 37° C. for 20 to 60 minutes. The cells are then washed with pre-warmed fresh medium that does not contain phenol red (37° C.) and observed using a Zeiss Axioplan epifluorescence microscope equipped with an appropriate filter set.

Example 22
Staining of lysosomes and mitochondria in living cells using an additional detection reagent
Cells prepared according to Example 19 are transfered to the labeling solution containing 75 nM Dye 3 and 75 nM of the mitochondrial stain MitoTracker CMXRos (Molecular Probes, Eugene Oreg.) and incubated at 37° C. for 30 minutes. The cells are then washed with fresh, pre-warmed culture medium that does not contain phenol red and examined under an epifluorescence microscope equipped with multibandpass filter set, such as an XF56 filter set (Omega Optical). As both dyes are organelle-specific, the lysosomes and other acidic organelles stain are stained a bright fluorescent green, while the mitochondria are simultaneously stained fluorescent red. No cross staining of organelles, indicated by a yellow fluorescent signal, is observed.

Example 23
Staining of fungal vacuoles
A sample of fungal cells is resuspended at $10^6$ cells/mL in 10 mL HEPES buffer, pH7.4, containing 5% glucose. A labeling solution of the desired dye (as prepared in Example 19) is added to the fungal cell suspension, to a final dye concentration of 10 μM. The cells are incubated at room temperature for a maximum of 3 to 5 minutes. The stained cells are pelleted by centrifugation and resuspended in fresh 10 mM HEPES buffer, pH 7.4, containing 5% glucose. The cells are then examined with a Zeiss microscope equiped with an appropriate filter set. The commonly used vacuole marker, 2',7'-dichlorodihydrofluorescein diacetate, can be used as a control for verifying the specificity of vacuolar staining.

Example 24
Staining acrosomes in sperm cells

A semen sample is diluted in HEPES-buffered isotonic saline solution containing serum albumin (10 mM HEPES, 0.85% NaCl, 10% BSA, pH 7.4). The sample is kept at 36° C. A 1 μM stock solution of the desired dye is prepared in the same buffer. A 100 μL aliquot of the stock solution is added to 900 μL of diluted semen, resulting in a final dye concentration of 100 nM. The sample is incubated with the dye for 20–30 minutes at 36° C. The sample is then observed using a fluorescent microscope equipped with a proper filter set (based on the excitation/emission wavelength of the dye used). Alternatively, the sample is analyzed and sorted using flow cytometry.

Example 25
Detection of an additional detection reagent in lysosomes

CPAE cells are incubated for 30 minutes in a solution of culture medium and 100 μg/mL *Datura stramonium* (jimson weed) lectin conjugated to fluorescein at 37° C. in a tissue culture incubator. This green fluorescent lectin has been shown to be taken up by live cells and trafficked to lysosomes. The cells are rinsed twice in fresh culture medium at 37° C., and then are allowed to recover in culture medium without lectin for 4 hours at 37° C. Following recovery, the cells are incubated with 100 nM Dye 43 and diluted in growth medium for 30 minutes at 37° C. The cells are then rinsed in growth medium without phenol red and mounted in the same.

Observation of the stained sample reveals red fluorescent and yellow fluorescent structures within the cells. The observed yellow fluorescence indicates colocalization of the green fluorescent lectin conjugate with the red dye of the invention in lysosomes. The red structures indicate the staining of acidic organelles that are not lysosomes.

Example 26
Detection of a foreign gene product in lysosomes

As lysosomes are the principal sites of intracellular digestion, there are some 40 acidic hydrolytic enzymes contained in lysosomes. There are also a plurality of different proteins present on the lysosomal membrane that play important roles in critical processes, including material transportation and H$^+$ pumping into the lumen. Both classes of lysosomal proteins are synthesized in the rough endoplasmic reticulum and transported through the Golgi apparatus. The precursors of all lysosomal hydrolases therefore carry a unique marker in the form of a mannose 6-phosphate (M6P) group, which will target the proteins for transport to lysosomes specifically.

By following the same protein import principle, a researcher can clone a gene sequence and manipulate it in such a way that the final product, a polypeptide, will fuse with the N-terminal first 100 amino acid residues of a regular lysosomal hydrolytic enzyme (L1). This fusion protein should have a M6P group and therefore target the lysosomes in transformed cells in a culture. The fusion protein can then be detected using immunocytochemical methods in combination with the dyes of the present invention. The typical procedure for the expression and detection of a foreign gene products in lysosomes of transformed cells comprises the following steps:

A specific protein with a known amino acid sequence (for example, a subunit of yeast protein: T1) is selected, and monoclonal antibodies (McAb) directed against that sequence are prepared. The selected DNA sequence coded for Y1 from a yeast cDNA library is amplified using the polymerase-chain reaction. The selected DNA sequence is then fused with amplified, selected bovine nuclear DNA, which codes for the first 100 amino acids of a bovine lysosomal protein (L1). Thus the fused gene has the proper sequence to encode a polypeptide with a correct N-terminal amino acid sequence that (1) will be modified by the addition of M6P group in the Golgi network and (2) lead the T1/L1 fusion protein into transformed bovine cell lysosomes.

The fused gene is ligated into a mammalian expression vector, such as pCI (Promega), which has the proper enhancer/promoter and other signal regions for accurate, high efficiency gene expression in bovine cells. A mammalian transfection system is used to transfer the gene construct into cultured bovine cells, establishing a stable, transformed cell line that expresses lysosomal targeting polypeptide T1/L1. The transformed cells are cultured under proper conditions.

The cells are stained with 150 nM of Dye 43 at 37° C. for 30 minutes. The lysosomes in the living cells are well labeled and fluoresce bright red. The stained cells are then fixed in 3.0% formaldehyde/0.5% glutaraldehyde for 20 min at room temperature and permeabilized with cold acetone for 10 min. Dye 43 is well retained in lysosomes throughout this cytochemical process.

In order to detect the special gene product, the sample cells are further incubated with McAb against T1. The immunocomplexes are detected with FITC-labeled secondary antibodies. Those regions of the sample showing both red fluorescence (lysosomes) and green fluorescence (immunocomplexes) indicate the antibody complex colocalizes in the lysosomes of the sample.

Example 27
The effect of NH$_3$ alkalization on acidic organellar staining in live cells Cell samples prepared according to Example 19 are transferred to two tissue culture dishes. The cells in the first dish are pre-incubated with 1 mM NH$_4$OH for 30 minutes at 37° C. The cells are then washed with fresh medium. The cells in both dishes are then incubated with a labeling solution that is 75 nM in Dye 3 (as described in Example 2) at 37° C. for 30 minutes. The cells are then washed with pre-warmed fresh medium and observed using a Zeiss Axioplan microscope equipped with an appropriate filter set.

The cells that were not initially alkalinized display good staining, with all of the lysosomes and other acidic organelles exhibiting a bright green fluorescence. The initially alkalinized cells, however, show only weak staining of acidic organelles, displaying less than 10% of the fluorescence intensity of the control cells.

Example 28
Triple labeling of lysosomes, Golgi apparatus and nuclei in living cells A cell sample prepared according to Example 19 are transferred to a tissue culture dish and incubated at 37° C. for 30 minutes in a labeling solution that is 75 nM in Dye 3 (as described in Example 2), 100 nM in BODIPY TR labeled ceramide (Molecular Probes, Inc., Eugene Oreg.) and 30 nM in Hoechst 33258 (Molecular Probes, Inc., Eugene Oreg.). The cells are then washed with fresh, pre-warned culture medium and examined under a Zeiss Axioplan microscope equipped with an appropriate filter set. The stained cells display green fluorescent acidic organelles, red fluorescent Golgi apparatus, and blue fluorescent nuclei.

Example 29
Analysis of cell viability/cytotoxicity

A cell sample prepared according to Example 19 is incubated at 37° C. for 30 minutes in a labeling solution that is 75 nM in Dye 3 and 50 nM in propidium iodide. The stained cells are then washed with fresh, pre-warmed culture medium. The cells are examined under a Zeiss Axioplan microscope equipped with an appropriate filter set. Dead cells exhibit fluorescent red nuclei, while live cells exhibit green fluorescent acidic organelles. Cells that have damaged (i.e. permeant) cell membranes, yet retain an acidic pH gradient with their acidic organelles will display both green and red fluorescence.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula

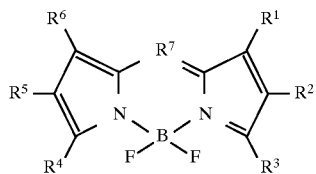

wherein $R^7$ is nitrogen, a methine or a methine that is substituted by halomethyl, cyano, alkyl, perfluoroalkyl, alkenyl, alkynyl, cycloalkyl, arylalkyl, acyl, aryl, heteroaryl; or LINK-CAP;

$R^1$–$R^6$, which may be the same or different, are hydrogen, halogen, cyano, alkyl, perfluoroalkyl, alkoxy, cycloalkyl, arylalkyl, acyl, aryl, heteroaryl, alkenyl or alkynyl; or LINK-CAP;

or where $R^7$ is not nitrogen, any two adjacent substituents of $R^1$, $R^2$, $R^3$, $R^4$, $R^5$ and $R^6$, taken in combination, form a fused aromatic 6-membered ring that is optionally and independently substituted by halogen, cyano, alkyl, perfluoroalkyl, alkoxy, alkenyl, alkynyl, cycloalkyl, alkylthio, alkylamido, amino, monoalkylamino, dialkylamino, carboxamide, hydroxy, mercapto, aryl, heteroaryl, aryl-amido, heteroaryl-amido, aryl-oxy, heteroaryl-oxy, aryl-amino, heteroaryl-amino, LINK-CAP, or that is substituted by 1–2 additional fused benzo or heteroaromatic rings that are optionally further substituted by halogen, amino, carboxamide, or LINK-CAP;

wherein any of said aryl, heteroaryl, aryl-amido, heteroaryl-amido, aryl-oxy, heteroaryl-oxy, aryl-amino or heteroaryl-amino substituents are optionally and independently substituted by halogen, amino, carboxamide, hydroxy or mercapto;

any of said alkenyl or alkynyl substituents independently has 2–6 carbons, and is optionally substituted by halogen, alkyl, cyano, carboxylate ester, carboxamide, aryl, heteroaryl, or additional alkenyl or alkynyl groups;

any alkyl substituent or alkyl portion of a substituent independently has 1–6 carbons, and is optionally substituted by halogen, amino, carboxamide, hydroxy or mercapto;

provided that at least one of $R^1$–$R^6$ is a LINK-CAP or is substituted by a LINK-CAP, or $R^7$ is a LINK-CAP substituted methine, and where the compound is substituted by more than one LINK-CAP, they are the same or different;

where LINK is a single covalent bond, or LINK is a covalent linkage having 1–20 nonhydrogen atoms selected from the group consisting of C, N, O and S, such that the linkage contains any combination of bonds selected from the group consisting of ether, thioether, amine, ester, carboxamide, sulfonamide or hydrazide bonds; single, double, triple or aromatic carbon-carbon bonds; aromatic or heteroaromatic bonds;

where CAP is —$CR^8R^9$—$NR^{10}R^{11}$;

where $R^8$ and $R^9$ are independently hydrogen or an alkyl having 1–6 carbons that is linear or branched, unsubstituted or optionally substituted by halogen, carboxamide, hydroxy, mercapto, cyano, or an amine that is optionally substituted by 0–2 alkyls independently having 1–6 carbons; or one of $R^8$ and $R^9$, when taken in combination with the LINK moiety, forms a 6- to 8-membered ring;

$R^{10}$ and $R^{11}$ are independently a linear or branched alkyl having 1–6 carbons; or $R^{10}$ and $R^{11}$ taken in combination form a saturated heterocycle that is a pyrrolidine, a piperidine, a piperazine, morpholine, an imidazole, an azepine or an oxazepine; or $R^{10}$ and $R^{11}$, when taken in combination with $R^8$ and $R^9$, or when taken in combination with the LINK moiety, forms a 5- or 6-membered nitrogen heterocycle that is a substituted pyrrolidine or piperidine.

2. A compound, as claimed in claim 1, wherein no two adjacent substituents of $R^1$, $R^2$, $R^3$, $R^4$, $R^5$ and $R^6$, taken in combination, form a fused aromatic 6-membered ring.

3. A compound, as claimed in claim 2, wherein each of $R^1$–$R^6$ that is not a LINK-CAP is independently hydrogen, halogen, alkyl alkenyl, aryl or heteroaryl.

4. A compound, as claimed in claim 2, wherein LINK has the formula —$(CH_2)_a(CONH(CH_2)_b)_z$—, where a is 0–5, b is 1–5 and z is 0 or 1.

5. A compound, as claimed in claim 2, where $R^{10}$ and $R^{11}$ are alkyl having 1–2 carbons.

6. A compound, as claimed in claim 1, having the formula

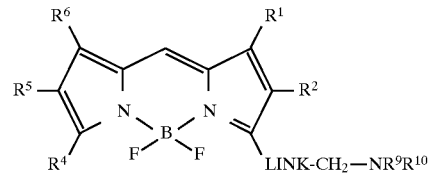

wherein $R^1$ is hydrogen;

$R^2$ and $R^5$ are independently H, Br, or I;

$R^4$ and $R^6$ are independently hydrogen, alkyl, aryl, heteroaryl, alkenyl or alkynyl;

$R^9$ and $R^{10}$ are alkyl having 1–2 carbons.

7. A compound, as claimed in claim 6, wherein $R^2$ and $R^5$ are each H or Br;

$R^4$ and $R^6$ are independently hydrogen, alkyl, phenyl, pyrrolyl, pyridyl, thienyl, ethenyl, or butadienyl; and LINK is —$(CH_2)_2$—$(CONH)$—$(CH_2)$—.

8. A method of staining acidic organelles, comprising:

a) combining a sample that comprises isolated acidic organelle, or a cell or cells containing acidic organelles, with one or more compounds of the formula

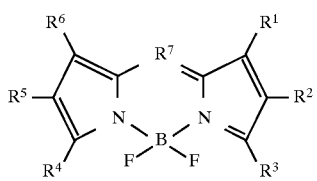

wherein R⁷ is nitrogen, a methine or a methine that is substituted by halomethyl, cyano, alkyl, perfluoroalkyl, alkenyl, alkynyl, cycloalkyl, arylalkyl, acyl, aryl, heteroaryl; or LINK-CAP;

R¹–R⁶, which may be the same or different, are hydrogen, halogen, cyano, alkyl, perfluoroalkyl, alkoxy, cycloalkyl, arylalkyl, acyl, aryl, heteroaryl, alkenyl or alkynyl; or LINK-CAP;

or where R⁷ is not nitrogen, any two adjacent substituents of R¹, R², R³, R⁴, R⁵ and R⁶, taken in combination, form a fused aromatic 6-membered ring that is optionally and independently substituted by halogen, cyano, alkyl, perfluoroalkyl, alkoxy, alkenyl, alkynyl, cycloalkyl, alkylthio, alkylamido, amino, monoalkylamino, dialkylamino, carboxamide, hydroxy, mercapto, aryl, heteroaryl, aryl-amido, heteroaryl-amido, aryl-oxy, heteroaryl-oxy, aryl-amino, heteroaryl-amino, LINK-CAP, or that is substituted by 1–2 additional fused benzo or heteroaromatic rings that are optionally further substituted by halogen, amino, carboxamide, or LINK-CAP;

wherein any of said aryl, heteroaryl, aryl-amido, heteroaryl-amido, aryl-oxy, heteroaryl-oxy, aryl-amino or heteroaryl-amino substituents are optionally and independently substituted by halogen, amino, carboxamide, hydroxy or mercapto; any of said alkenyl or alkynyl substituents independently has 2–6 carbons, and is optionally substituted by halogen, alkyl, cyano, carboxylate ester, carboxamide, aryl, heteroaryl, or additional alkenyl or alkynyl groups;

any alkyl substituent or alkyl portion of a substituent independently has 1–6 carbons, and is optionally substituted by halogen, amino, carboxamide, hydroxy or mercapto;

provided that at least one of R¹–R⁶ is a LINK-CAP or is substituted by a LINK-CAP, or R⁷ is a LINK-CAP substituted methine, and where the compound is substituted by more than one LINK-CAP, they are the same or different;

where LINK is a single covalent bond, or LINK is a covalent linkage having 1–20 nonhydrogen atoms selected from the group consisting of C, N, O and S, such that the linkage contains any combination of bonds selected from the group consisting of ether, thioether, amine, ester, carboxamide, sulfonamide or hydrazide bonds; single, double, triple or aromatic carbon-carbon bonds; aromatic or heteroaromatic bonds;

where CAP is —CR⁸R⁹—NR¹⁰R¹¹;

where R⁸ and R⁹ are independently hydrogen or an alkyl having 1–6 carbons that is linear or branched, unsubstituted or optionally substituted by halogen, carboxamide, hydroxy, mercapto, cyano, or an amine that is optionally substituted by 0–2 alkyls independently having 1–6 carbons; or one of R⁸ and R⁹, when taken in combination with the LINK moiety, forms a 6- to 8-membered ring;

R¹⁰ and R¹¹ are independently a linear or branched alkyl having 1–6 carbons; or R¹⁰ and R¹¹ taken in combination form a saturated heterocycle that is a pyrrolidine, a piperidine, a piperazine, morpholine, an imidazole, an azepine or an oxazepine; or R¹⁰ and R¹¹, when taken in combination with R⁸ and R⁹, or when taken in combination with the LINK moiety, forms a 5- or 6-membered nitrogen heterocycle that is a substituted pyrrolidins or piperidine;

for a time sufficient to produce stained acidic organelles, where the concentration of said compound is sufficient to produce stained acidic organelles.

9. A method, as claimed in claim 8, wherein no two adjacent substituents of R¹, R², R³, R⁴, R⁵ and R⁶, taken in combination, form a fused aromatic 6-membered ring.

10. A method, as claimed in claim 9, wherein each of R¹–R⁶ is hydrogen, halogen, alkyl, alkenyl, aryl or heteroaryl.

11. A method, as claimed in claim 9, wherein R⁷ is an unsubstituted, alkyl substituted or LINK-CAP substituted methine.

12. A method, as claimed in claim 9, wherein LINK contains any combination of carbon-carbon single bonds and carboxamide bonds.

13. A method, as claimed in claim 9, wherein LINK contains 1–6 carbon atoms.

14. A method, as claimed in claim 9, wherein LINK has the formula —(CH₂)ₐ(CONH(CH₂)ᵦ)z-, where a is 0–5, b is 1–5 and z is 0 or 1.

15. A method, as claimed in claim 9, where R⁸ and R⁹ are H, and R¹⁰ and R¹¹ are independently H or alkyl having 1–6 carbons.

16. A method, as claim 15, where R¹⁰ and R¹¹ are alkyl having 1–2 carbons.

17. A method, as claimed in claim 8, wherein said compound or compounds are present in a labeling solution in a concentration greater than 20 nM and less than 400 nM.

18. A method, as claimed in claim 8, wherein said sample comprises a cell or cells.

19. A method, as claimed in claim 18, wherein said cell or cells are mammalian cells.

20. A method, as claimed in claim 19, wherein said cell or cells are sperm cells.

21. A method, as claimed in claim 18, wherein said cell or cells are yeast or plant cells.

22. A method, as claimed in claim 18, further comprising adding an additional detection reagent to said cell or cells.

23. A method, as claimed in claim 22, wherein said additional detection reagent is a mitochondrial stain or a nucleic acid stain.

24. A method, as claimed in claim 23, wherein said additional detection reagent is an antibody, a lectin, an avidin or a streptavidin.

25. A method, as claimed in claim 8, further comprising illuminating said sample with an excitation source at a wavelength greater than 450 nm.

26. A method, as claimed in claim 25, wherein said sample comprises a cell or cells that are abnormal cells.

27. A method, as claimed in claim 26, further comprising observing said cell or cells with means for detecting the fluorescence response in said cells.

28. A method, as claimed in claim 27, wherein the step of observing is performed using a microscope, fluorometer, microtiter plate reader, or flow cytometer.

29. A method, as claimed in claim 27, further comprising sorting said cell or cells based on the fluorescent response in said cells.

30. A method, as claimed in claim 8, wherein said sample comprises a mammalian cell or cells;

said compound is present in a labeling solution having a concentration greater than 20 nM and less than 400 nM; LINK has the formula $-(CH_2)_a(CONH(CH_2)_b)_z-$, where a is 0–5, b is 1–5 and z is 0 or 1; $R^{10}$ and $R^{11}$ are alkyl having 1–2 carbons; each of $R^1$–$R^6$ is hydrogen, halogen, alkyl alkenyl, aryl, or heteroaryl; and $R^7$ is an unsubstituted or alkyl substituted methine.

* * * * *

UNITED STATES PATENT AND TRADEMARK OFFICE
CERTIFICATE OF CORRECTION

PATENT NO. : 5,869,689
DATED : February 9, 1999
INVENTOR(S) : Zhang et al.

It is certified that error appears in the above-identified patent and that said Letters Patent is hereby corrected as shown below:

Column 7,
Table 1, Dye No. 26 "$(CH_2)_2CONH(CH_2)_2N$" should read -- $(CH_2)_2CONH(CH_2)_3N$ --.

Signed and Sealed this

Seventeenth Day of September, 2002

Attest:

Attesting Officer

JAMES E. ROGAN
*Director of the United States Patent and Trademark Office*